US012788368B2

(12) United States Patent
Morimoto et al.

(10) Patent No.: US 12,788,368 B2
(45) Date of Patent: Nov. 10, 2026

(54) ULTRASOUND ENDOSCOPE SYSTEM

(71) Applicant: FUJIFILM Corporation, Tokyo (JP)

(72) Inventors: Yasuhiko Morimoto, Ashigarakami-gun (JP); Kensuke Masui, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 19/076,989

(22) Filed: Mar. 11, 2025

(65) Prior Publication Data

US 2025/0302441 A1 Oct. 2, 2025

(30) Foreign Application Priority Data

Mar. 28, 2024 (JP) ................................ 2024-054726

(51) Int. Cl.
*A61B 8/00* (2006.01)
*A61B 8/12* (2006.01)

(52) U.S. Cl.
CPC .............. *A61B 8/4494* (2013.01); *A61B 8/12* (2013.01); *A61B 8/445* (2013.01); *A61B 8/4488* (2013.01); *A61B 8/5207* (2013.01)

(58) Field of Classification Search
CPC ..... A61B 1/00064; A61B 1/0055; A61B 1/04; A61B 8/4494; A61B 8/12; A61B 8/445; A61B 8/4488; A61B 8/5207; A61B 8/44; A61B 8/4416; A61B 8/5215; A61B 8/54
USPC ................................ 600/462, 459, 101–183
See application file for complete search history.

(56) References Cited

U.S. PATENT DOCUMENTS

| | | | | |
|---|---|---|---|---|
| 5,235,986 A * | 8/1993 | Maslak | G01S 15/8927 600/447 |
| 2006/0241473 A1* | 10/2006 | Kuniyasu | A61B 8/12 600/459 |
| 2010/0063392 A1* | 3/2010 | Nishina | A61B 8/4488 600/439 |
| 2011/0301413 A1* | 12/2011 | Morimoto | A61B 1/00087 600/104 |
| 2019/0239739 A1 | 8/2019 | Hiraoka | |
| 2022/0361846 A1 | 11/2022 | Hiraoka | |

FOREIGN PATENT DOCUMENTS

| | | |
|---|---|---|
| JP | 3152753 B2 * | 4/2001 |
| WO | 2018079792 | 5/2018 |
| WO | 2021161497 | 8/2021 |
| WO | 2021166985 | 8/2021 |

* cited by examiner

*Primary Examiner* — Boniface N Nganga
(74) *Attorney, Agent, or Firm* — JCIPRNET

(57) ABSTRACT

The ultrasound endoscope system includes: an ultrasound endoscope including a transducer array in which a plurality of transducers extending in a first direction intersecting an axial direction of an insertion part are arranged in a curved shape; and a processor configured to perform processing of generating an ultrasound image based on an output signal of the transducer array obtained by controlling the transducer array, in which an opening angle of the transducer array as viewed in the first direction is 90 degrees or more and less than 180 degrees, and the processor is configured to perform first control of generating the ultrasound image with a first angle of view larger than the opening angle.

25 Claims, 14 Drawing Sheets

ULTRASOUND ENDOSCOPE SYSTEM

CROSS-REFERENCE TO RELATED APPLICATIONS

The present application claims priority under 35 U.S.C. § 119 to Japanese Patent Application No. 2024-054726 filed on Mar. 28, 2024. The above application is hereby expressly incorporated by reference, in its entirety, into the present application.

BACKGROUND OF THE INVENTION

1. Field of the Invention

The technology of the present disclosure relates to a system.

2. Description of the Related Art

WO2021/161497A, WO2018/079792A, and WO2021/166985A describe convex type ultrasound endoscopes.

SUMMARY OF THE INVENTION

An object of the present disclosure is to provide an ultrasound endoscope in which a distal end part can be reduced in size.

A system of an embodiment according to the technology of the present disclosure comprises: an ultrasound endoscope including a transducer array in which a plurality of transducers, each of which extends in a first direction intersecting an axial direction of an insertion part of the ultrasound endoscope, are arranged in a curved shape; and a processor configured to perform processing of generating an ultrasound image based on an output signal of the transducer array obtained by controlling the transducer array, in which an opening angle of the transducer array as viewed in the first direction is 90 degrees or more and less than 180 degrees, and the processor is configured to perform first control of generating the ultrasound image with a first angle of view which is larger than the opening angle.

According to the technology of the present disclosure, it is possible to provide an ultrasound endoscope in which a distal end part can be reduced in size.

DESCRIPTION OF THE PREFERRED EMBODIMENTS

Figure 1:
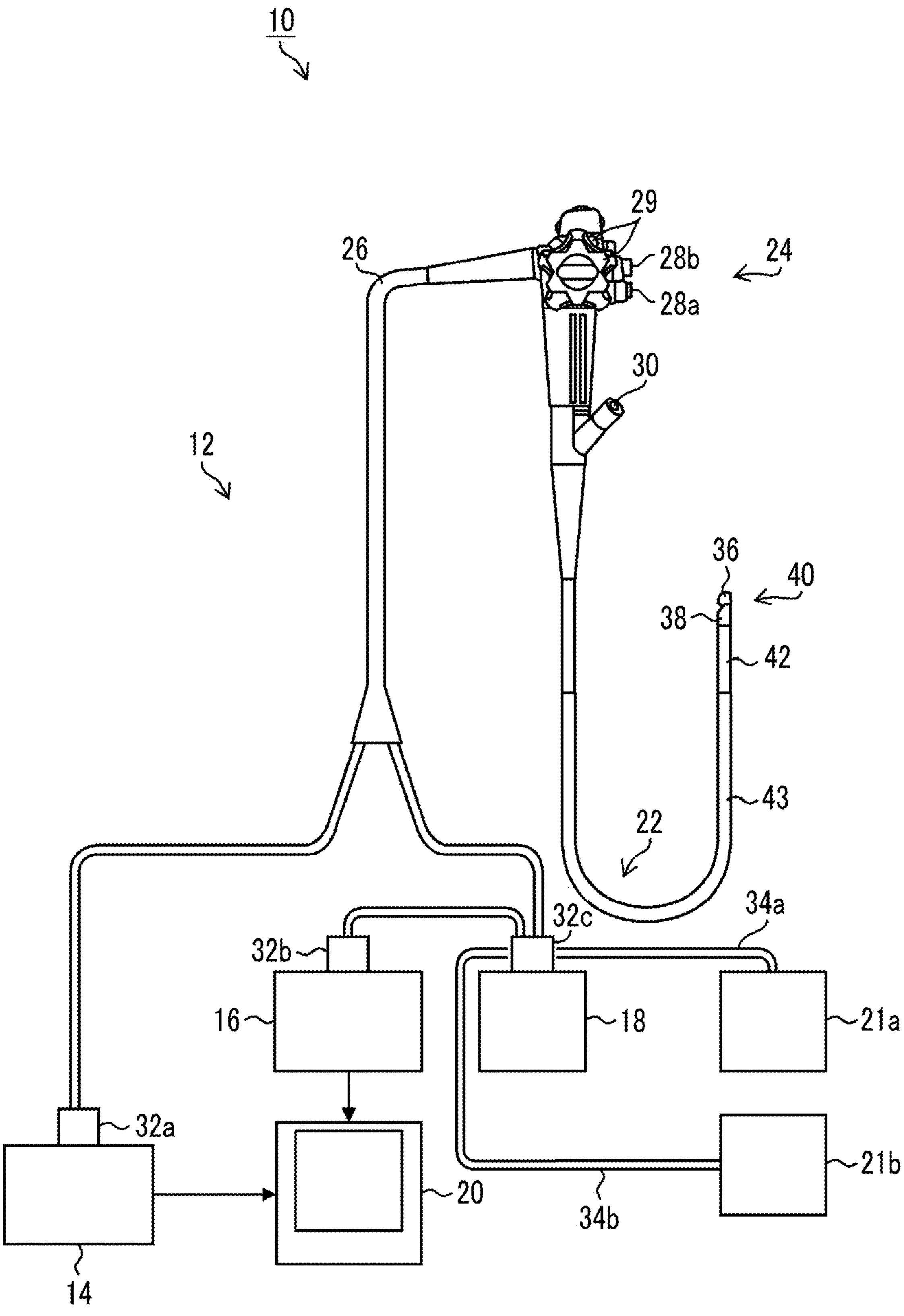
FIG. 1 is a schematic configuration diagram showing an example of an ultrasound examination system 10 using an ultrasound endoscope 12 according to an embodiment of the technology of the present disclosure.

FIG. 1 is a schematic configuration diagram showing an example of an ultrasound examination system 10 using an ultrasound endoscope 12 according to an embodiment of the technology of the present disclosure. The ultrasound examination system 10 constitutes a system. The ultrasound examination system 10 comprises the ultrasound endoscope 12, an ultrasound processor device 14 that generates an ultrasound image, an endoscope processor device 16 that generates an endoscopic image, a light source device 18 that supplies illumination light for illuminating an inside of a body cavity to the ultrasound endoscope 12, a monitor 20 that displays the ultrasound image and the endoscopic image, a water supply tank 21*a* that stores cleaning water and the like, and a suction pump 21*b* that suctions an object to be suctioned in the body cavity.

The ultrasound endoscope 12 has an insertion part 22 that is inserted into a body cavity of a subject, an operating part 24 that is continuously provided in a proximal end part of the insertion part 22 and that is used by an operator to perform an operation, and a universal cord 26 that has one end connected to the operating part 24.

In the operating part 24, an air/water supply button 28*a* that opens and closes an air/water supply pipe line (not shown) from the water supply tank 21*a*, and a suction button 28*b* that opens and closes a suction pipe line (not shown) from the suction pump 21*b* are provided side by side. In the operating part 24, a pair of angle knobs 29 and a treatment tool insertion port 30 are provided.

At the other end of the universal cord 26, an ultrasound connector 32*a* that is connected to the ultrasound processor device 14, an endoscope connector 32*b* that is connected to the endoscope processor device 16, and a light source connector 32*c* that is connected to the light source device 18 are provided. The ultrasound endoscope 12 is attachably and detachably connected to the ultrasound processor device 14, the endoscope processor device 16, and the light source device 18 via the connectors 32*a*, 32*b*, and 32*c*, respectively. The connector 32*c* comprises an air/water supply tube 34*a* that is connected to the water supply tank 21*a*, and a suction tube 34*b* that is connected to the suction pump 21*b*.

The insertion part 22 has, in order from a distal end side, a distal end part 40 having an ultrasound observation part 36 and an optical observation part 38, a bendable part 42 that is continuously provided on a proximal end side of the distal end part 40, and a flexible part 43 that connects a proximal end side of the bendable part 42 and a distal end side of the operating part 24.

The bendable part 42 is remotely operated to be bent by rotatably operating the pair of angle knobs 29 provided in the operating part 24. As a result, the distal end part 40 can be directed in a desired direction.

The ultrasound processor device 14 includes various processors that perform processing of generating an ultrasound image based on an output signal (echo signal reflected from an observation target site to which ultrasound is emitted) of a transducer array 50 obtained by controlling the transducer array 50 of the ultrasound observation part 36.

The various processors include a central processing unit (CPU) that is a general-purpose processor executing a program to perform various types of processing, a programmable logic device (PLD) that is a processor of which a circuit configuration can be changed after manufacture such as a field-programmable gate array (FPGA), or a dedicated electrical circuit that is a processor having a circuit configuration designed to be dedicated to executing specific processing such as an application-specific integrated circuit (ASIC). More specifically, a structure of these various processors is an electrical circuit in which circuit elements such as semiconductor elements are combined.

The ultrasound processor device 14 may be configured by one of the various processors, or by a combination of two or more processors of the same type or different types (for example, a combination of a plurality of FPGAs or a combination of a CPU and an FPGA).

The endoscope processor device 16 receives and acquires a captured image signal acquired from the observation target site illuminated with the illumination light from the light source device 18 in the optical observation part 38, and performs various types of processing on the acquired captured image signal to generate an endoscopic image displayed on the monitor 20.

In the example of FIG. 1, the ultrasound processor device 14 and the endoscope processor device 16 are configured with two devices (computers) provided separately. However, the present invention is not limited thereto, and both the ultrasound processor device 14 and the endoscope processor device 16 may be configured by one device.

In order to image an observation target site inside a body cavity using the optical observation part 38 to acquire a captured image signal, the light source device 18 generates illumination light, such as white light including light of three primary colors of red light, green light, and blue light or light of a specific wavelength. The illumination light propagates through a light guide (not shown) and the like in the ultrasound endoscope 12 and is emitted from an illumination window 70 (see FIGS. 2 and 3) of the optical observation part 38 to illuminate the observation target site inside the body cavity.

The monitor 20 receives video signals generated by the ultrasound processor device 14 and the endoscope processor device 16 and displays the ultrasound image and the endoscopic image. In regard to the display of the ultrasound image and the endoscopic image, only one of these images may be appropriately switched and displayed on the monitor 20 or both images may be displayed simultaneously.

In the present embodiment, although the ultrasound image and the endoscopic image are displayed on one monitor 20, a monitor for ultrasound image display and a monitor for endoscopic image display may be provided separately. In addition, the ultrasound image and the endoscopic image may be displayed in a display form other than the monitor 20, for example, in a form of being displayed on a display of a terminal carried by the operator.

Figure 2:
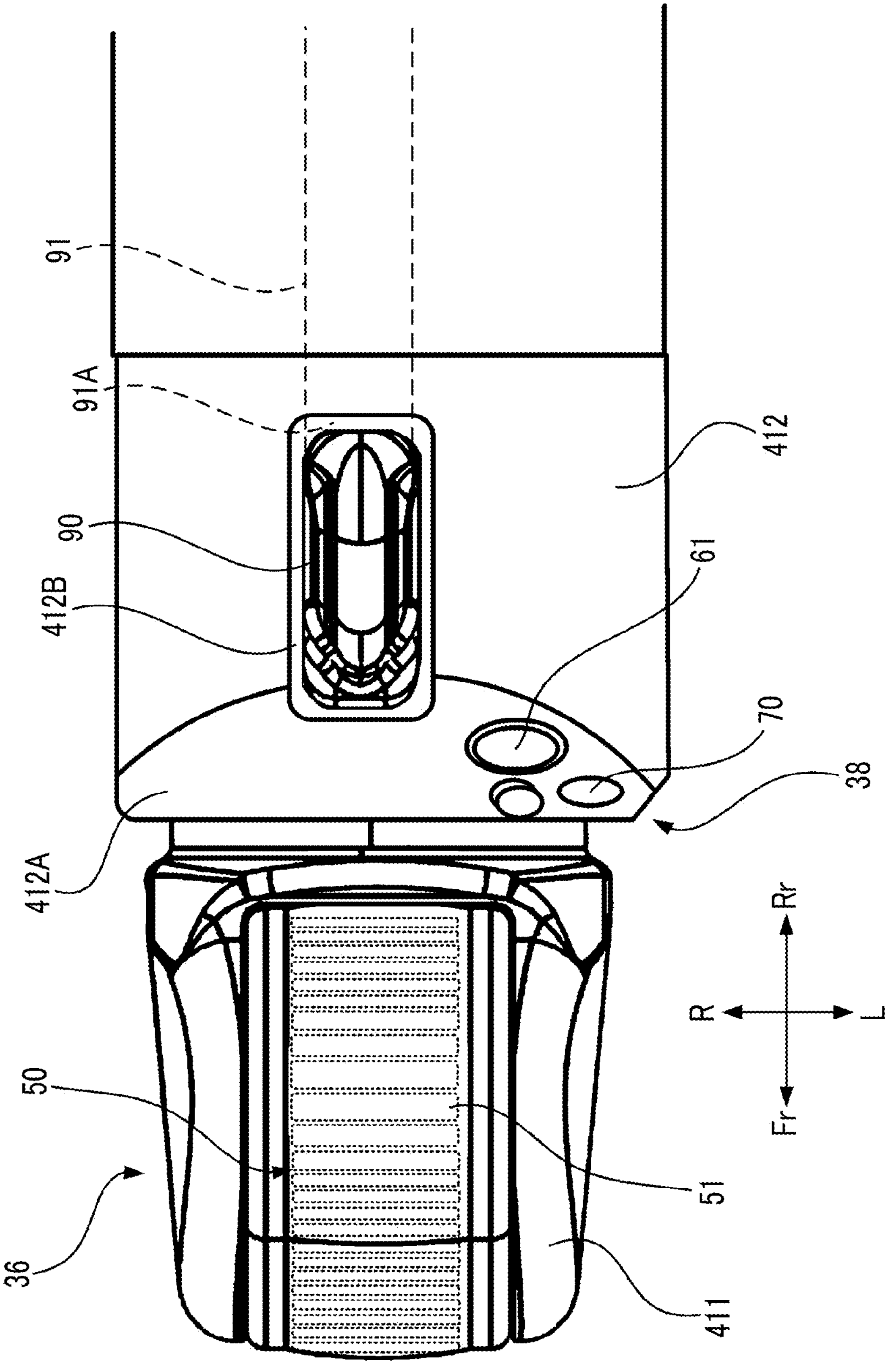
FIG. 2 is a partially enlarged plan view of a distal end part 40 shown in FIG. 1.
Figure 3:
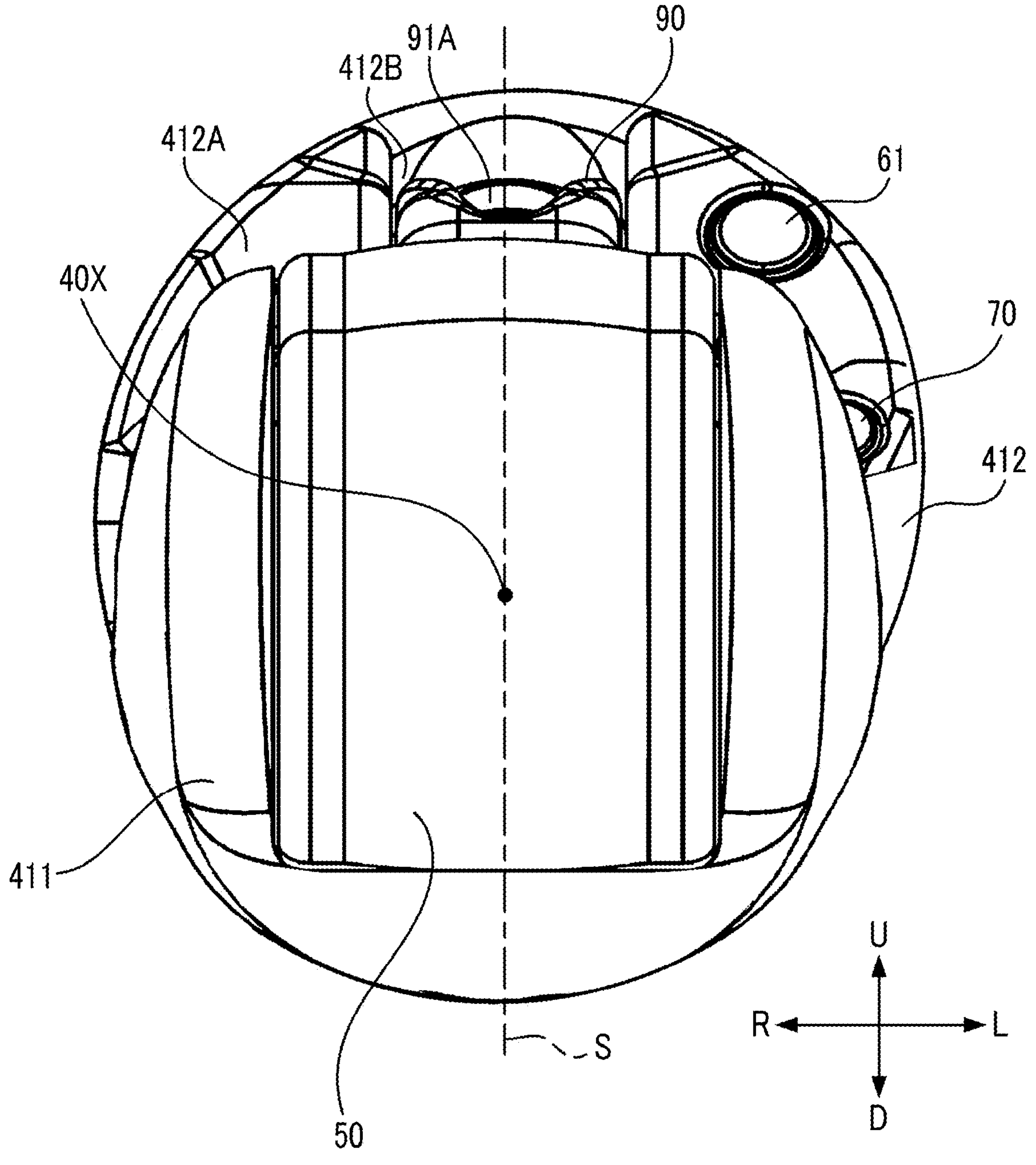
FIG. 3 is a front view of the distal end part 40 shown in FIG. 2 as viewed from a distal end side.
Figure 4:
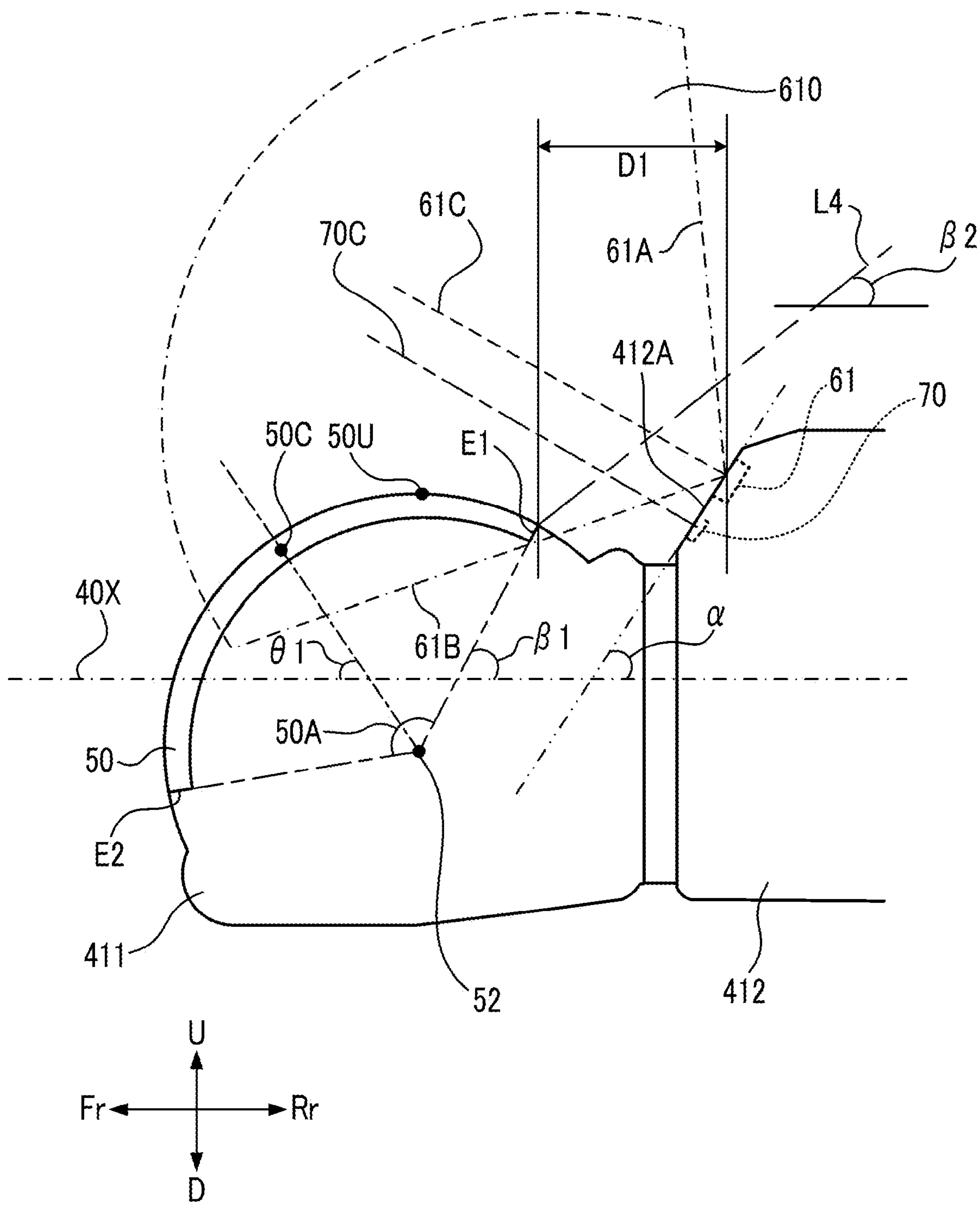
FIG. 4 is a side view of the distal end part 40 shown in FIG. 2 as viewed from a right side.

FIG. 2 is a partially enlarged plan view of the distal end part 40 shown in FIG. 1. FIG. 2 shows a direction from a proximal end side to the distal end side (hereinafter, referred to as a distal end direction Fr) and a direction from the distal end side to the proximal end side (hereinafter, referred to as a proximal end direction Rr) as an axial direction of the insertion part 22. The distal end direction Fr and the proximal end direction Rr will also be collectively referred to as an axial direction. In addition, a right direction R and a left direction L which is opposite to the right direction R are shown as directions orthogonal to the axial direction. The right direction R and the left direction L will also be collectively referred to as a right-left direction. The right-left direction constitutes a first direction intersecting the axial direction. In the following description, one of directions orthogonal to the axial direction and the right-left direction, from which ultrasound is emitted, is referred to as an upward direction U, and the other direction is referred to as a downward direction D. The upward direction U and the downward direction D will also be collectively referred to as an up-down direction. FIG. 3 is a front view of the distal end part 40 shown in FIG. 2 as viewed from the distal end side. FIG. 4 is a side view of the distal end part 40 shown in FIG. 2 as viewed from a right side.

As shown in FIG. 2, in the distal end part 40, the ultrasound observation part 36 for acquiring an ultrasound image, the optical observation part 38 for acquiring an endoscopic image, and an outlet port 91A of a treatment tool such as a puncture needle are arranged in this order from the distal end side. An exterior body of the distal end part 40 comprises a first exterior body 411 and a second exterior body 412 provided on a proximal end side of the first exterior body 411. The first exterior body 411 is provided with the ultrasound observation part 36. The second exterior body 412 is provided with the optical observation part 38, a raising base 90 of the treatment tool, and the outlet 91A which is an outlet of a treatment tool insertion path 91 that is provided to extend from the treatment tool insertion port 30 to an inside of the insertion part 22.

The optical observation part 38 comprises an imaging module 60 including an observation window 61, the illumination window 70 formed of transparent resin, glass, or the like that emits light from the light guide, a signal cable 80 (see FIG. 5), and the like.

Figure 5:
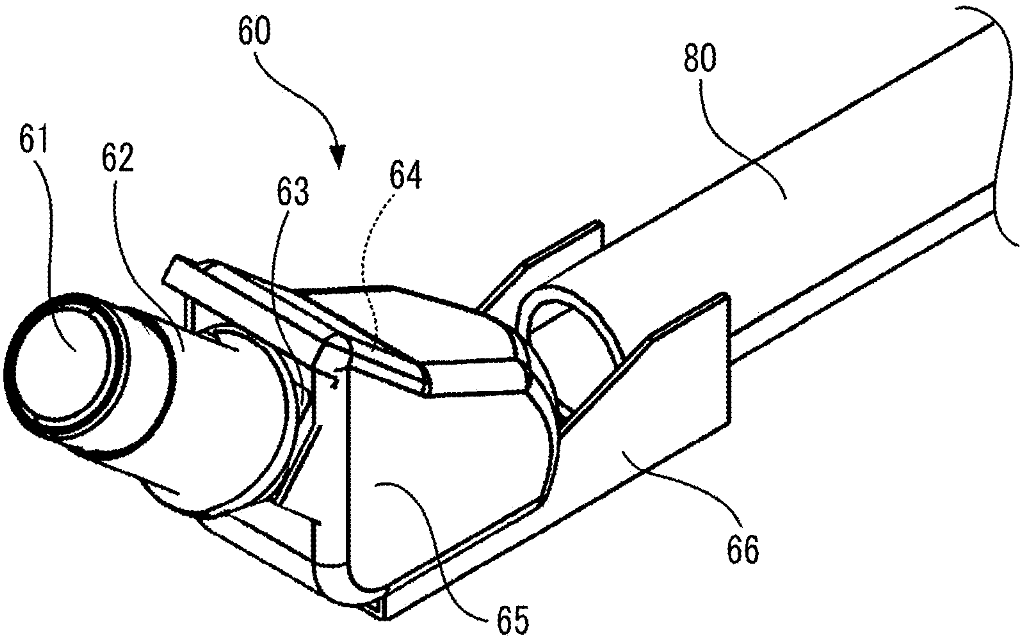
FIG. 5 is a perspective view schematically showing an imaging module 60 and a signal cable 80.

FIG. 5 is a perspective view schematically showing the imaging module 60 and the signal cable 80. The imaging module 60 comprises a cylindrical lens barrel 62 that supports a lens group including an objective lens constituting the observation window 61, a prism 63 that bends a direction of subject light passing through the lens group of the lens barrel 62 at a right angle, an imaging element 64 that is disposed to face a light-emitting surface of the prism 63, a mounting substrate (not shown) of the imaging element 64 that is provided on a rear surface of the imaging element 64, a holder 65 that integrally supports the lens barrel 62, the prism 63, the imaging element 64, and the mounting substrate, and a cable support part 66 that is fixed to the holder 65. The cable support part 66 supports the signal cable 80 that is electrically connected to various substrates included in the imaging module 60. The signal cable 80 extends to the connector 32*b* and is connected to the endoscope processor device 16.

The lens barrel 62 and the lens group inside the lens barrel 62 constitute an imaging optical system. The prism 63, the imaging element 64, and the mounting substrate of the imaging element 64 constitute an imaging unit that performs imaging through the imaging optical system. Here, the prism 63 is used due to the disposition of the imaging element 64, but the prism 63 is not essential and can be omitted.

As shown in FIG. 4, in the second exterior body 412, a distal end surface 412A of an upper end part is an inclined surface that is inclined toward the proximal end side with respect to an axis 40X of the insertion part 22. As shown in FIG. 2, the observation window 61 and the illumination window 70 are provided on the distal end surface 412A. The observation window 61 is provided in a hole portion 420 (see FIG. 12) provided in the distal end surface 412A, and a main plane of the observation window 61 is substantially parallel to the distal end surface 412A. As described above, the observation window 61 is provided to be inclined toward the proximal end side with respect to the axis 40X.

FIG. 3 shows a division line S that passes through the axis 40X and that extends in the up-down direction. As shown in FIG. 3, in a case where the distal end part 40 is divided into two parts on the left and right by the division line S as the distal end part 40 is viewed from the distal end side, both the observation window 61 and the illumination window 70 are disposed in a left divided region. In other words, in the front view of FIG. 3, the observation window 61 is provided eccentric to the left direction L, and the illumination window 70 is provided eccentric to the same left direction L as the observation window 61.

As shown in FIG. 2, a rectangular recess portion 412B is provided on an upper surface of the second exterior body 412 on the proximal end side with respect to the observation window 61. A side surface of the recess portion 412B on the proximal end side is provided with the outlet port 91A. The raising base 90 is supported inside the recessed portion 412B. The raising base 90 is supported to be raised in the upward direction U with an end part of the raising base 90 on the proximal end side as a fulcrum. The raising base 90 is not essential and can be omitted.

The ultrasound observation part 36 has the transducer array 50 in which a plurality of transducers 51 having a rectangular parallelepiped shape extending in the right-left direction are arranged in a curved shape. As shown in FIG. 4, the transducer array 50 is arranged in a convex arc shape toward an outside. FIG. 4 shows a center of curvature 52 at which distances from the respective transducers 51 included in the transducer array 50 are the same. The transducers 51 included in the transducer array 50 are arranged on an arc of a circle having the center of curvature 52 as a center and the shortest distance as a radius.

In a side view of FIG. 4, one end edge E1 of the transducer array 50 having a convex arc shape is located on the proximal end side with respect to the center of curvature 52, and the other end edge E2 is located on the distal end side with respect to the center of curvature 52. In the present specification, an angle formed by a line segment connecting the center of curvature 52 and the one end edge E1 and a line segment connecting the center of curvature 52 and the other end edge E2 is defined as an opening angle 50A of the transducer array 50.

The opening angle 50A is 90 degrees or more and less than 180 degrees. Since the opening angle 50A is 90 degrees or more and less than 180 degrees, an ultrasound beam can be scanned over a sufficiently wide range, and a size (for example, length in the axial direction) of the first exterior body 411 can be reduced. In a case where the size of the first exterior body 411 is reduced, even in a case where the distal end part 40 is brought close to a site of the subject in a state in which the site of the subject is observed through the observation window 61, the transducer array 50 can be prevented from coming into contact with the site. Furthermore, since a length of the distal end part is shortened, operability is improved and a burden on the subject during the operation is reduced. In consideration of compatibility between a size of a scanning range of the ultrasound beam required for the ultrasound image and the reduction in size of the distal end part 40, the opening angle 50A is preferably set to 140 degrees or more and 160 degrees or less.

The number of the transducers 51 (the number of channels) included in the transducer array 50 is preferably set to 96 or more in order to obtain a sufficient resolution of the ultrasound image, and is preferably set to 128 or less in order to reduce the size of the distal end part 40. Compared to an ultrasound endoscope having a transducer array in which the opening angle 50A is 180 degrees and the number of channels is 96 or more and 128 or less, according to the present aspect, a density of the transducers 51 in the transducer array 50 can be increased as the opening angle 50A is reduced, and image quality of the ultrasound image can be improved.

FIG. 4 shows an inclination angle α of the distal end surface 412A with respect to the axis 40X. The inclination angle α constitutes a second angle. In addition, FIG. 4 shows an angle θ1 formed by a straight line connecting a center 50C and a center of curvature 52 in an arrangement direction of the transducers 51 in the transducer array 50 and the axis 40X. The angle θ1 constitutes a fourth angle. Assuming an actual use environment of the ultrasound endoscope, the angle θ1 (fourth angle) is preferably set to 45 degrees or more and 55 degrees or less, and the inclination angle α (second angle) is preferably set to 35 degrees or more and 50 degrees or less.

FIG. 4 shows an observation visual field 610 of the observation window 61. The observation visual field 610 is a range of a subject that can be imaged with an appropriate image quality by the imaging module 60. The observation visual field 610 is defined in a range surrounded by an observation range upper limit 61A that defines an end on one side from an optical axis 61C of the observation window 61 and an observation range lower limit 61B that defines an end on the other side from the optical axis 61C of the observation window 61. The optical axis 61C corresponds to a center of the observation visual field 610. An angle of the observation visual field 610 (corresponding to an angle of view of the imaging module 60) is preferably equal to or less than the opening angle 50A, and more preferably 120 degrees or more and 140 degrees or less.

As shown in FIG. 4, the other end edge E2 of the transducer array 50 is disposed below the axis 40X, and the one end edge E1 of the transducer array 50 is disposed above the axis 40X. FIG. 4 shows an upper end edge 50U of the transducer array 50. The upper end edge 50U constitutes one end edge of the transducer array 50 in the up-down direction. In the example of FIG. 4, the one end edge E1 is located on the proximal end side with respect to the upper end edge 50U, the other end edge E2 is located on the distal end side with respect to the upper end edge 50U, and the center 50C is located on the distal end side with respect to the upper end edge 50U.

It is preferable that the upper end edge 50U is included in the observation visual field 610. In other words, it is preferable that the observation range lower limit 61B of the observation visual field 610 is located below the upper end edge 50U and that the observation range upper limit 61A of the observation visual field 610 is located above the upper end edge 50U. In this way, even in a case where a length of the first exterior body 411 in the axial direction is reduced, the imaging module 60 can image the vicinity of the upper end edge 50U of the transducer array 50 together with the subject, and the site of the subject can be observed while checking a position of the transducer array 50.

In addition, as shown in FIG. 4, it is preferable that the center 50C of the transducer array 50 is located between the observation range upper limit 61A and the observation range lower limit 61B. The observation range upper limit 61A and the observation range lower limit 61B can also be referred to as rays constituting both ends of the observation visual field 610. In a configuration of the example of FIG. 4, the observation range lower limit 61B is located below the center 50C. In this way, even in a case where the observation visual field 610 is changed due to an assembly error of the imaging module 60 in the ultrasound endoscope 12 or the like, the vicinity of the upper end edge 50U of the transducer array 50 can be disposed at an appropriate position of the captured image.

In addition, as shown in FIG. 4, it is preferable that the optical axis 61C of the observation window 61 is located above the upper end edge 50U. In this way, it is easy to place the site of the subject facing the center 50C in the center of the captured image, and the operability of the transducer array 50 can be improved.

FIG. 4 shows a distance D1 in the front-rear direction between the one end edge E1 and the observation window 61. The distance D1 is preferably set to 10 mm or less in order to shorten the length of the distal end part 40.

It is preferable that a center line 70C of the illumination window 70 is located above the one end edge E1. In this way, in a case of imaging the upper end edge 50U of the transducer array 50 and the site of the subject beyond the upper end edge 50U, the site of the subject can be sufficiently illuminated, and brightness of the captured image can be ensured.

The ultrasound processor device 14 performs first driving control and second driving control as driving control of the transducer array 50. Hereinafter, the first driving control and the second driving control will be described.

Figure 6:
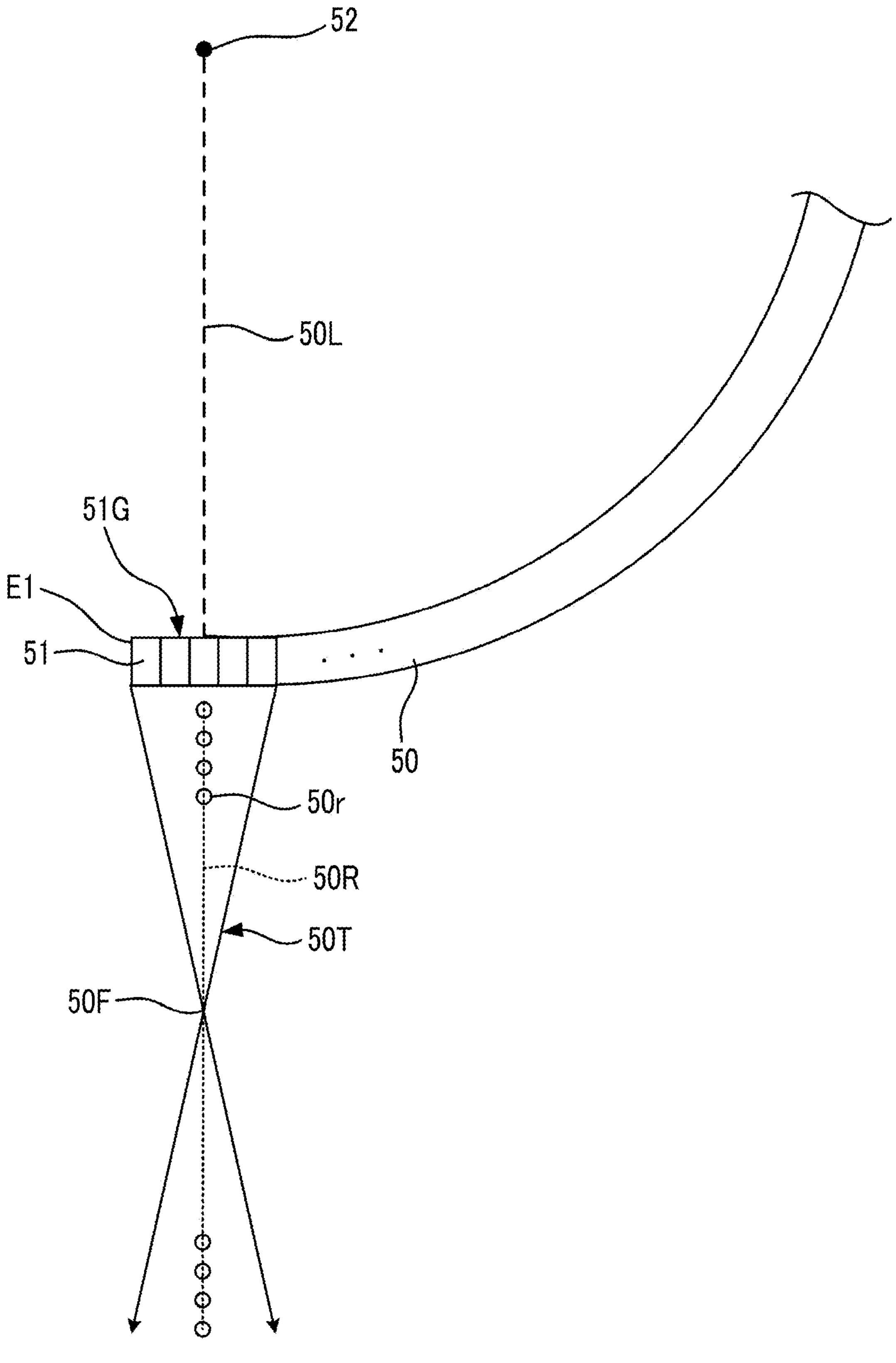
FIG. 6 is a schematic diagram for describing second driving control of a transducer array 50.

FIG. 6 is a schematic diagram for describing the second driving control of the transducer array 50. FIG. 6 shows a state in which the curved transducer array 50 is viewed in the right-left direction.

The ultrasound processor device 14 forms a ultrasound beam 50T by using the plurality of (five in the example of FIG. 6) transducers 51 arranged continuously as a transducer group 51G and exciting the transducers 51 belonging to the transducer group 51G with a predetermined delay relationship. The ultrasound beam 50T has a transmission focal point 50F formed at a set depth. In the second driving control shown in FIG. 6, the ultrasound beam 50T is formed such that the transmission focal point 50F is located on an extension line of a straight line 50L connecting the transducer 51 at the center among the plurality of transducers 51 included in the transducer group 51G and the center of curvature 52. In the ultrasound beam 50T, a side (upper side) shallower than the transmission focal point 50F and a side (lower side) deeper than the transmission focal point 50F gradually widen. In FIG. 6, the ultrasound beam 50T is schematically illustrated.

In a case where a reflected wave of the ultrasound beam 50T is received by the transducer group 51G, a reception signal group is obtained from the transducer group 51G. The ultrasound processor device 14 processes the reception signal group to obtain a reception data group 50R. The reception data group 50R consists of a plurality of pieces of reception data (echo data) 50*r* corresponding to a plurality of reception points (sample points) arranged on the extension line of the straight line 50L. In this way, the reception data group 50R is obtained by one transducer group 51G. By performing the same driving control while shifting the position of the transducer 51 at the center included in the transducer group 51G one by one, a plurality of the reception data groups 50R corresponding to one scanning surface, that is, one frame, are obtained.

In the present specification, a propagation direction of the ultrasound beam 50T from which the reception data group 50R is obtained is defined as a direction in which a plurality of reception points corresponding to the reception data group 50R are arranged. In the second driving control shown in FIG. 6, the ultrasound processor device 14 performs the driving control of the transducer group 51G such that a direction (this direction constitutes a third direction) connecting the transducer 51 at the center among the plurality of transducers 51 included in the transducer group 51G and the center of curvature 52 and the propagation direction of the ultrasound beam 50T (the direction in which the reception data 50*r* are arranged) coincide with each other.

Figure 7:
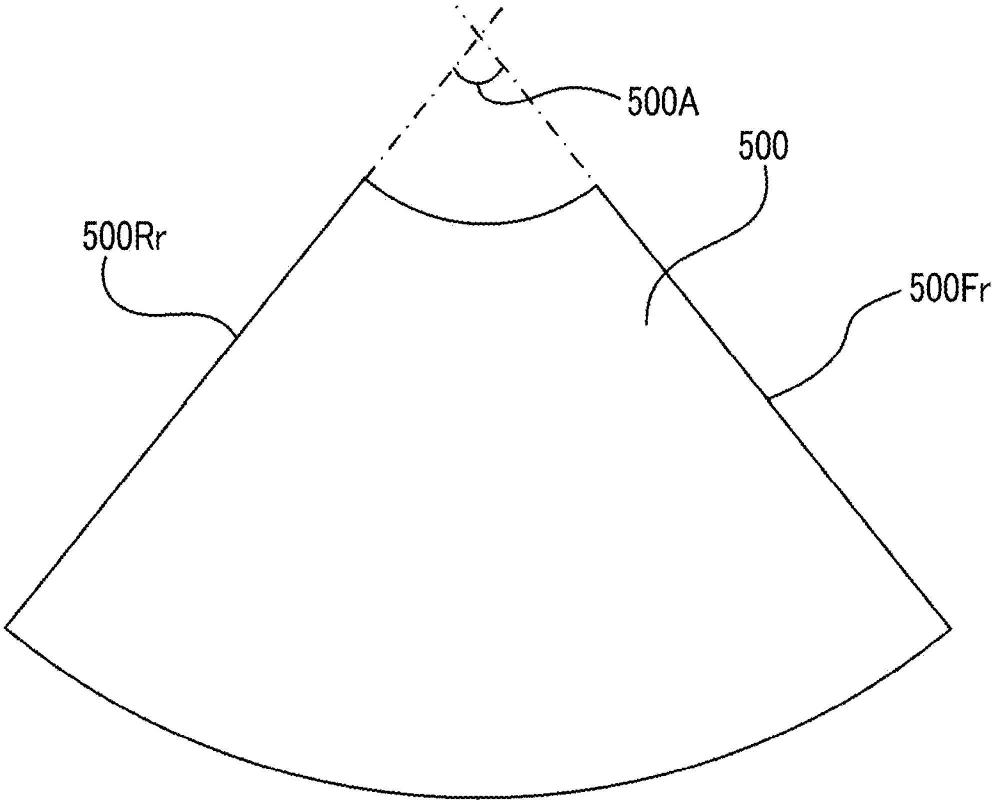
FIG. 7 is a schematic diagram showing an example of an ultrasound image based on a reception data group 50R obtained in a case where the second driving control shown in FIG. 6 is performed on all transducer groups 51G set in the transducer array 50.

FIG. 7 is a schematic diagram showing an example of an ultrasound image based on a reception data group 50R obtained in a case where the second driving control shown in FIG. 6 is performed on all the transducer groups 51G set in the transducer array 50.

An ultrasound image 500 includes an image line 500Rr corresponding to the reception data group 50R of the ultrasound beam 50T generated by the transducer group 51G closest to the one end edge E1 of the transducer array 50, and an image line 500Fr corresponding to the reception data group 50R of the ultrasound beam 50T generated by the transducer group 51G closest to the other end edge E2 of the transducer array 50, and image lines corresponding to the reception data groups 50R of the ultrasound beams 50T generated by the other transducer groups 51G are present between the image lines 500Rr and 500Fr. In the present specification, an angle formed by the image line 500Rr and the image line 500Fr is defined as an angle of view 500A of the ultrasound image 500. In a case where the second driving control is performed on all the transducer groups 51G set in the transducer array 50, the angle of view 500A is an angle slightly smaller than the opening angle 50A.

Figure 8:
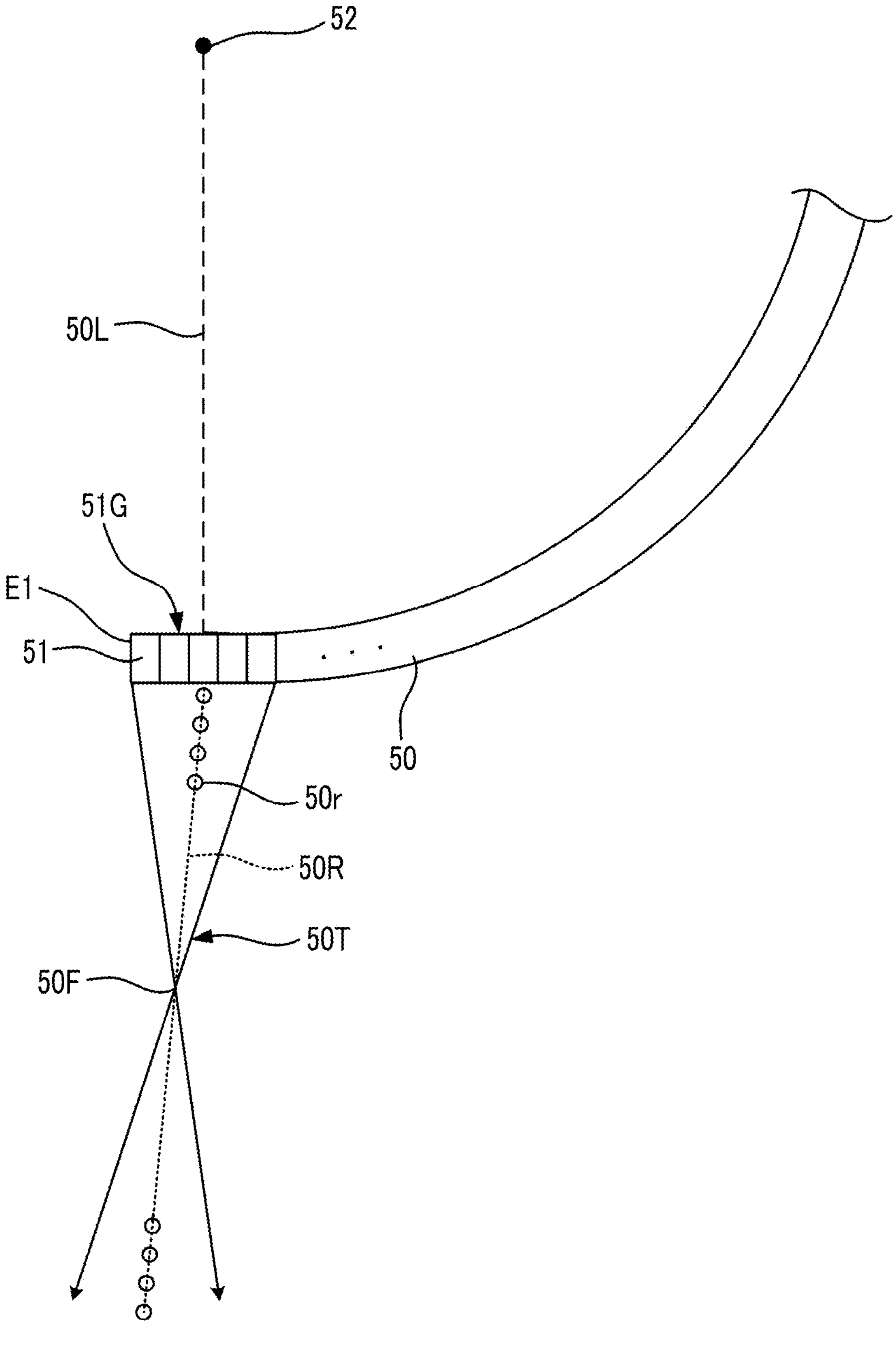
FIG. 8 is a schematic diagram for describing first driving control of the transducer array 50.

FIG. 8 is a schematic diagram for describing the first driving control of the transducer array 50. In the first driving control shown in FIG. 8, excitation timings of the plurality of transducers 51 included in the transducer group 51G are controlled to form the ultrasound beam 50T such that the transmission focal point 50F is located at a position deviated from the extension line of the straight line 50L in the arrangement direction of the transducers 51. Therefore, in the first driving control shown in FIG. 8, the propagation direction of the ultrasound beam 50T is a direction (this direction constitutes a second direction) intersecting the direction (third direction) connecting the transducer 51 at the center among the plurality of transducers 51 included in the transducer group 51G and the center of curvature 52. In the example of FIG. 8, the propagation direction of the ultrasound beam 50T is oriented toward a one end edge E1 side with respect to the direction (third direction) in which the straight line 50L extends. However, the propagation direction of the ultrasound beam 50T can also be oriented toward the other end edge E2 side with respect to the direction (third direction) in which the straight line 50L extends.

For example, by performing the first driving control (control of orienting the propagation direction of the ultrasound beam 50T toward the one end edge E1 side with respect to the direction in which the straight line 50L extends) on the transducer group 51G set at an end part of the transducer array 50 on the proximal end side and performing the second driving control on the other transducer groups 51G, a scanning range of ultrasound can be widened to the proximal end side compared to a case where the second driving control is performed on all the transducer groups 51G.

In addition, by performing the first driving control (control of orienting the propagation direction of the ultrasound beam 50T toward the other end edge E2 side with respect to the direction in which the straight line 50L extends) on the transducer group 51G set at an end part of the transducer array 50 on the distal end side and performing the second driving control on the other transducer groups 51G, the scanning range of the ultrasound can be widened to the distal end side compared to the case where the second driving control is performed on all the transducer groups 51G.

In addition, by performing the first driving control on the transducer group 51G set at both end parts of the transducer array 50 and performing the second driving control on the transducer group 51G set at another center portion (for example, a range of ±45 degrees from the center of the transducer array 50), the scanning range of the ultrasound can be widened to the proximal end side and the distal end side compared to the case where the second driving control is performed on all the transducer groups 51G.

The first driving control can also be performed on all the transducer groups 51G set in the transducer array 50. In this case, it is possible to widen the scanning range of the ultrasound to at least one of the proximal end side or the distal end side or to shift the scanning range of the ultrasound, compared to the case where the second driving control is performed on all the transducer groups 51G.

Figure 9:
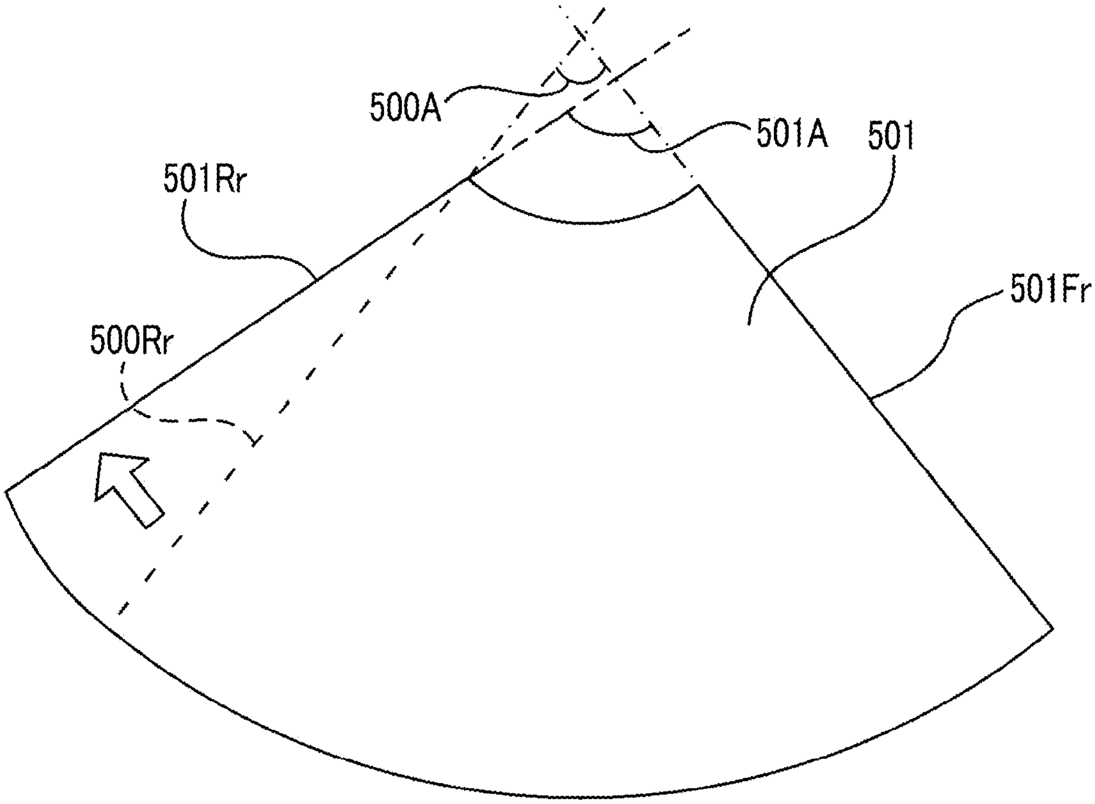
FIG. 9 is a schematic diagram showing an example of an ultrasound image 501 based on the reception data group 50R obtained in a case where the second driving control shown in FIG. 8 is performed on the transducer group 51G set at an end part of the transducer array 50 on one end edge E1 side.

FIG. 9 is a schematic diagram showing an example of an ultrasound image 501 based on the reception data group 50R obtained in a case where the second driving control shown in FIG. 8 is performed on the transducer group 51G set at the end part of the transducer array 50 on the one end edge E1 side.

The ultrasound image 501 includes an image line 501Rr corresponding to the reception data group 50R obtained from the transducer group 51G closest to the one end edge E1 of the transducer array 50 and an image line 501Fr corresponding to the reception data group 50R obtained from the transducer group 51G closest to the other end edge E2 of the transducer array 50, and image lines corresponding to the reception data groups 50R obtained from the other transducer groups 51G are present between the image lines 501Rr and 501Fr. An angle formed by the image line 501Rr and the image line 501Fr is an angle of view 501A of the ultrasound image 501. The ultrasound image 501 is wider on the proximal end side than the ultrasound image 500 by the number of image lines corresponding to a part in the transducer array 50 on which the first driving control is performed (a region of the transducer array 50 that generates the ultrasound image of a part beyond the opening angle 50A).

The angle of view 501A is larger than the angle of view 500A. The angle of view 501A can be made larger than the opening angle 50A. It is preferable that the opening angle 50A is set to 140 degrees or more and 160 degrees or less in order to reduce the size of the distal end part 40 and to ensure the scanning range of the ultrasound. However, even in a case where the opening angle 50A is set in this range, it is possible to obtain the same usability as the ultrasound endoscope in which the opening angle 50A is 180 degrees, as long as an ultrasound image having an angle of view of approximately 180 degrees can be generated. From such a viewpoint, the angle of view 501A is preferably set to be larger than the opening angle 50A by 15 degrees or more, and is preferably set to 180 degrees or less.

As described above, the ultrasound processor device 14 performs first control of generating the ultrasound image with a first angle of view (the angle of view 501A in the example of FIG. 9) larger than the opening angle 50A, and second control of generating the ultrasound image with a second angle of view (the angle of view 500A in the example of FIG. 7) smaller than the first angle of view. In the first control, the ultrasound processor device 14 performs at least the first driving control out of the first driving control and the second driving control on the transducer array 50. In the second control, the ultrasound processor device 14 performs the second driving control on the entire transducer array 50. The first control can also be referred to as control of performing sector scanning of shifting a phase of a transmission pulse applied to each of the plurality of transducers 51 included in the transducer group 51G on at least a part of the transducer array 50. In the first control, it is preferable that an angle formed by the propagation direction of the ultrasound beam 50T generated from the transducer group 51G (a direction in which a straight line indicating the reception data group 50R in FIG. 8 extends) and the straight line 50L increases closer to an end edge of the transducer array 50. In a case where the second control is to perform the second driving control on the entire transducer array 50, the second control can be referred to as control of performing convex scanning for observing a visual field substantially the same as the opening angle 50A.

It is preferable that the first control and the second control can be switched by operating a button or the like provided in the operating part 24. It is preferable that the ultrasound processor device 14 displays any one of the ultrasound image obtained by the first control or the ultrasound image obtained by the second control on the monitor 20, and further displays information indicating which control the ultrasound image is obtained by on the monitor 20. The ultrasound processor device 14 may return to the first control after a certain time has elapsed after a change from the first control to the second control by the operation of the operating part 24, without receiving the operation of the operating part 24. On the contrary, the ultrasound processor device 14 may return to the second control after a certain time has elapsed after a change from the second control to the first control by the operation of the operating part 24, without receiving the operation of the operating part 24.

Figure 10:
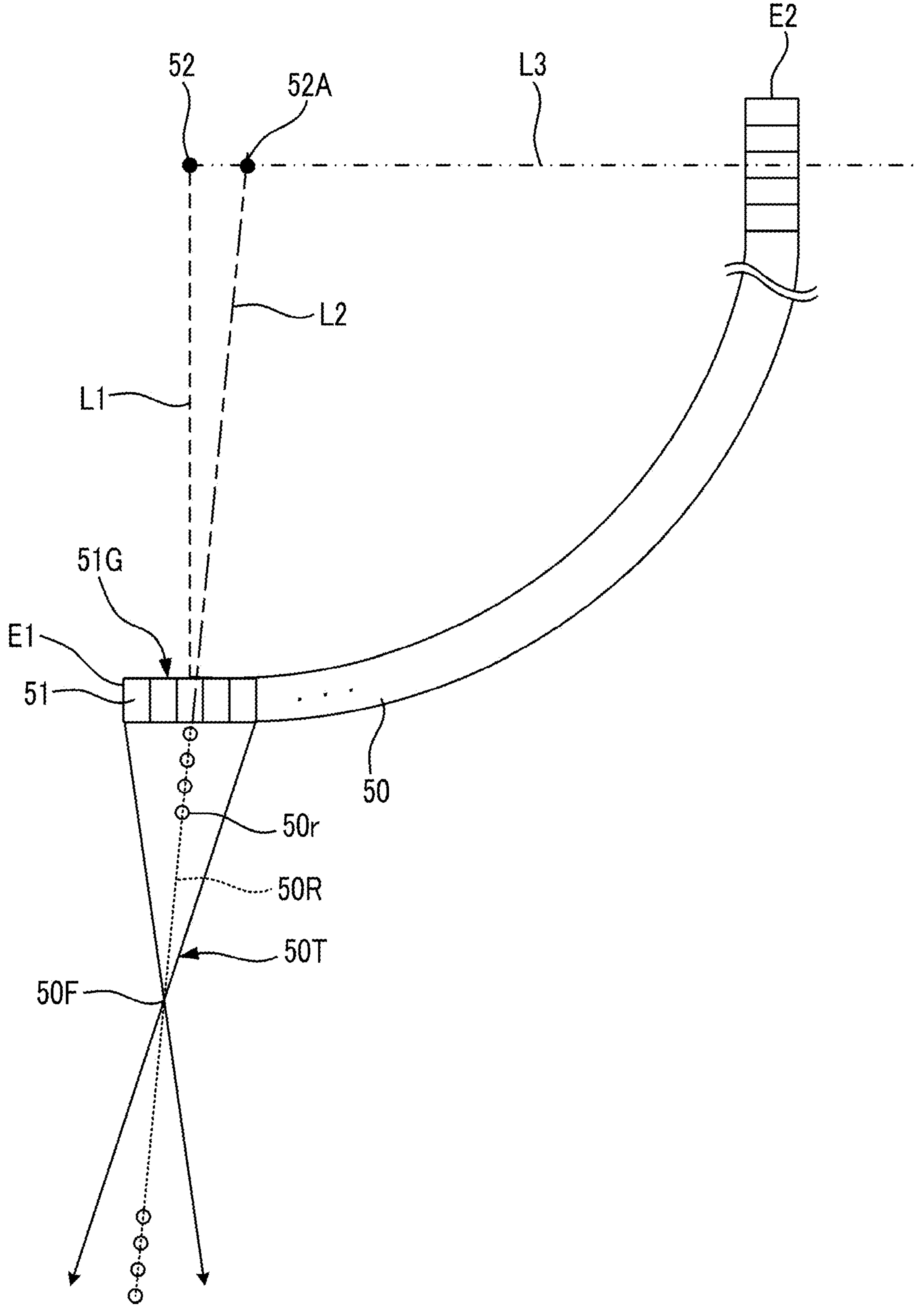
FIG. 10 is a schematic diagram illustrating a state of an ultrasound beam in a case where the first driving control is performed on the transducer group 51G set at an end part of the transducer array 50 on a proximal end side and the second driving control is performed on the other transducer groups 51G.

FIG. 10 is a schematic diagram illustrating a state of the ultrasound beam in a case where the first driving control is performed on the transducer group 51G set at the end part of the transducer array 50 on the proximal end side and the second driving control is performed on the other transducer groups 51G.

A straight line L2 shown in FIG. 10 indicates an extension line of a straight line connecting the transducer 51 at the center of the transducer group 51G closest to the one end edge E1 of the transducer array 50 and the transmission focal point 50F of the ultrasound beam 50T generated from the transducer group 51G. A straight line L3 shown in FIG. 10 indicates an extension line of a straight line connecting the transducer 51 at the center of the transducer group 51G closest to the other end edge E2 of the transducer array 50 and the transmission focal point 50F of the ultrasound beam 50T generated from the transducer group 51G. A straight line L1 shown in FIG. 10 indicates an extension line corresponding to the straight line L2 in a case where the second driving control is performed on the transducer group 51G closest to the one end edge E1 of the transducer array 50.

An intersection point of the straight line L1 and the straight line L3 coincides with the center of curvature 52. An intersection 52A of the straight line L2 and the straight line L3 is shifted to a position closer to a propagation direction side of the ultrasound beam than the center of curvature 52. As described above, a position of the intersection point of the straight line L1 and the straight line L3 corresponding to both end edges of the ultrasound image in a case of performing the second control and a position of the intersection point of the straight line L2 and the straight line L3 corresponding to both end edges of the ultrasound image in a case of performing the first control are different.

FIG. 4 shows an angle β1 formed by the line segment connecting the one end edge E1 and the center of curvature 52 and the axis 40X. The angle β1 constitutes a first angle. It is preferable that the angle β1 is equal to or greater than the inclination angle α (second angle). In this way, the observation window 61 and the raising base 90 can be disposed close to the one end edge E1 of the transducer array 50, and a treatment using the treatment tool can be satisfactorily performed.

In addition, FIG. 4 shows a straight line L4 indicating, in a case where the first driving control is performed on the transducer group 51G closest to one end edge E1, a propagation direction of an ultrasound beam (hereinafter, referred to as a first ultrasound beam) sent out from the transducer group 51G and an angle β2 formed by the straight line L4 and the axis 40X. The angle β2 constitutes a third angle. It is preferable that the inclination angle α (second angle) is equal to or greater than the angle β2 (third angle). With such a configuration, blind spots of the observation window 61 can be reduced. In addition, it is preferable that the angle β2 (third angle) is set to an angle at which the straight line L4 does not intersect with the observation window 61. In this way, the first ultrasound beam can be prevented from being blocked by the observation window 61, and the angle of view of the ultrasound image can be greatly widened.

Figure 11:
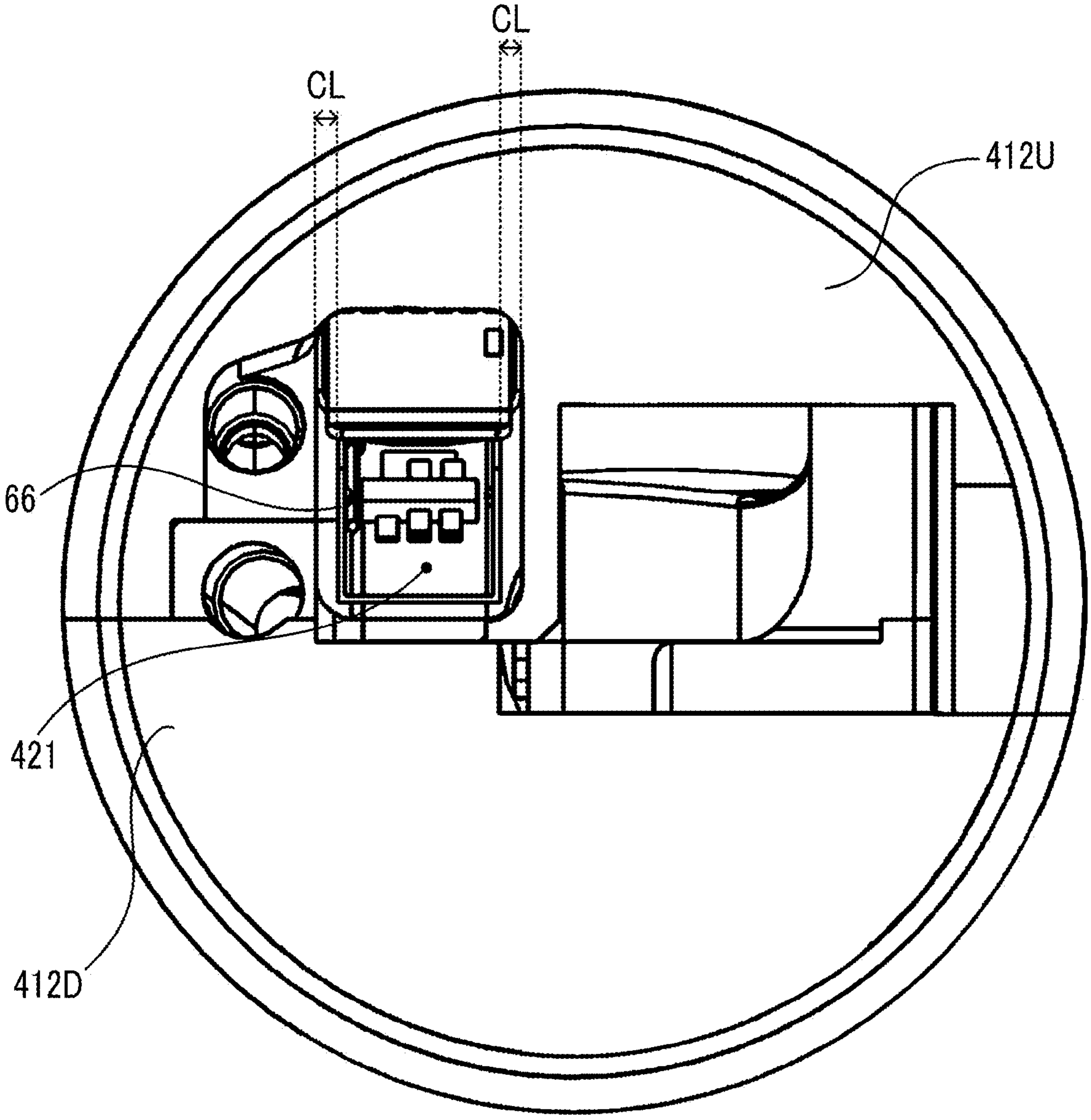
FIG. 11 is a view of an internal structure of a second exterior body 412 as viewed from the proximal end side.
Figure 12:
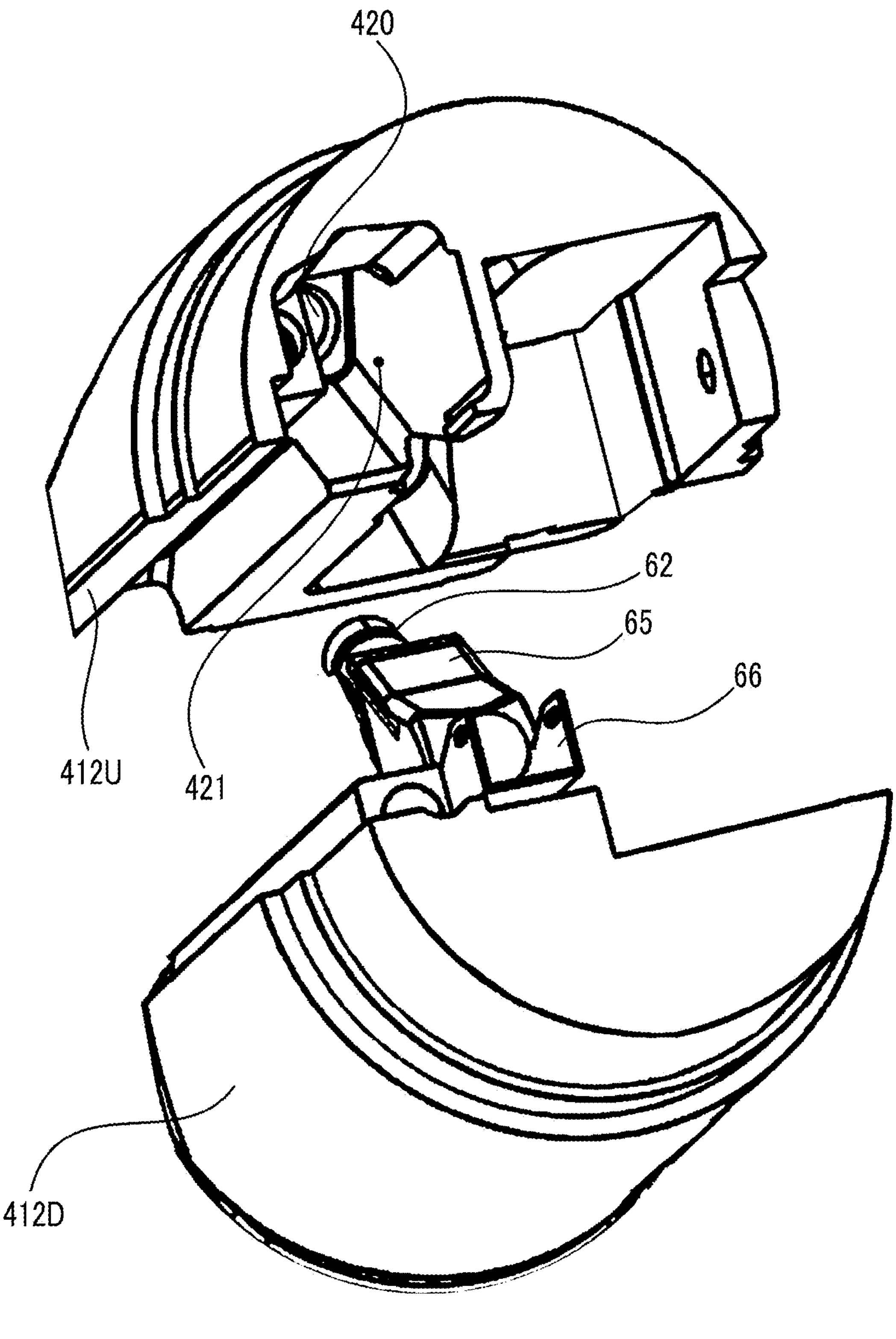
FIG. 12 is an exploded perspective view of the second exterior body 412 shown in FIG. 11.
Figure 13:
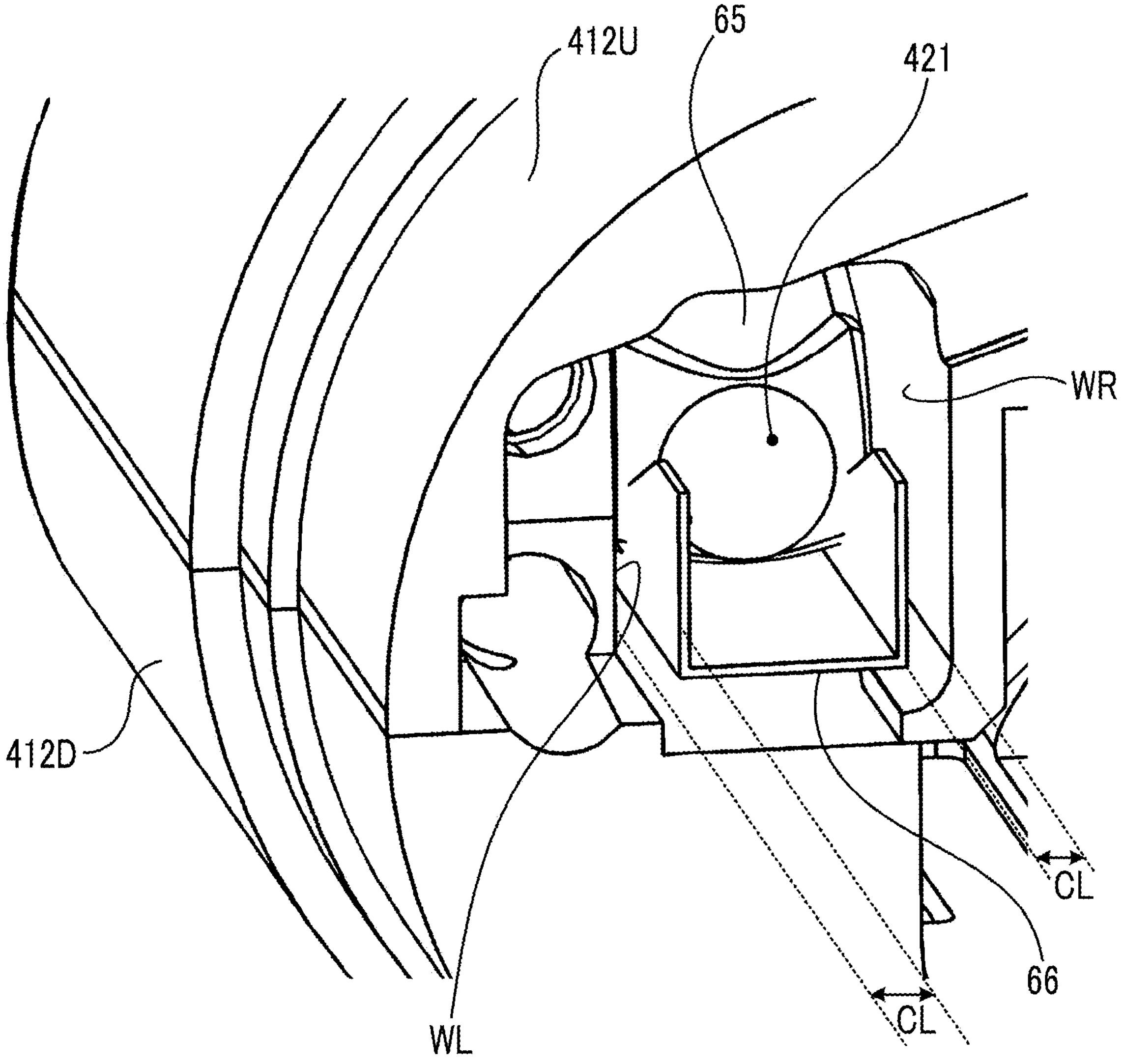
FIG. 13 is a partially enlarged perspective view showing FIG. 11.

FIG. 11 is a view of an internal structure of the second exterior body 412 as viewed from the proximal end side. FIG. 12 is an exploded perspective view of the second exterior body 412 shown in FIG. 11. FIG. 13 is a partially enlarged perspective view showing FIG. 11. In FIGS. 11 to 13, the signal cable 80 shown in FIG. 5 is not shown.

The second exterior body 412 is configured by connecting an upper member 412U and a lower member 412D. The holder 65 and the cable support part 66 of the imaging module 60 are accommodated in an accommodation space 421 having a substantially rectangular parallelepiped shape formed between the upper member 412U and the lower member 412D. The lens barrel 62 of the imaging module 60 is inserted into a columnar hole portion 420 that is provided to penetrate a wall surface on the distal end side and an upper side of the upper member 412U, the wall surface forming the accommodation space 421. A position (that is, a position in a radial direction) of the lens barrel 62 in a direction perpendicular to the optical axis of the observation window 61 is positioned at the hole portion 420. The lens barrel 62 is fixed to the hole portion 420 with an adhesive or the like in a state of being inserted into the hole portion 420. As described above, the imaging module 60 is supported by the second exterior body 412. The second exterior body 412 constitutes a support member that supports the imaging module 60.

The lens barrel 62 is rotatable around the optical axis of the observation window 61 in the hole portion 420 in a state before being inserted into the hole portion 420 and being fixed to the hole portion 420. In this state, the lens barrel 62 is configured not to be movable in the radial direction thereof in the hole portion 420. By rotating the lens barrel 62 in the hole portion 420, a position of the imaging element integrated with the lens barrel 62 can be changed. By rotating the lens barrel 62 in the hole portion 420, a position where the transducer array 50 shown in the captured image captured by the imaging element can be adjusted.

Figure 14:
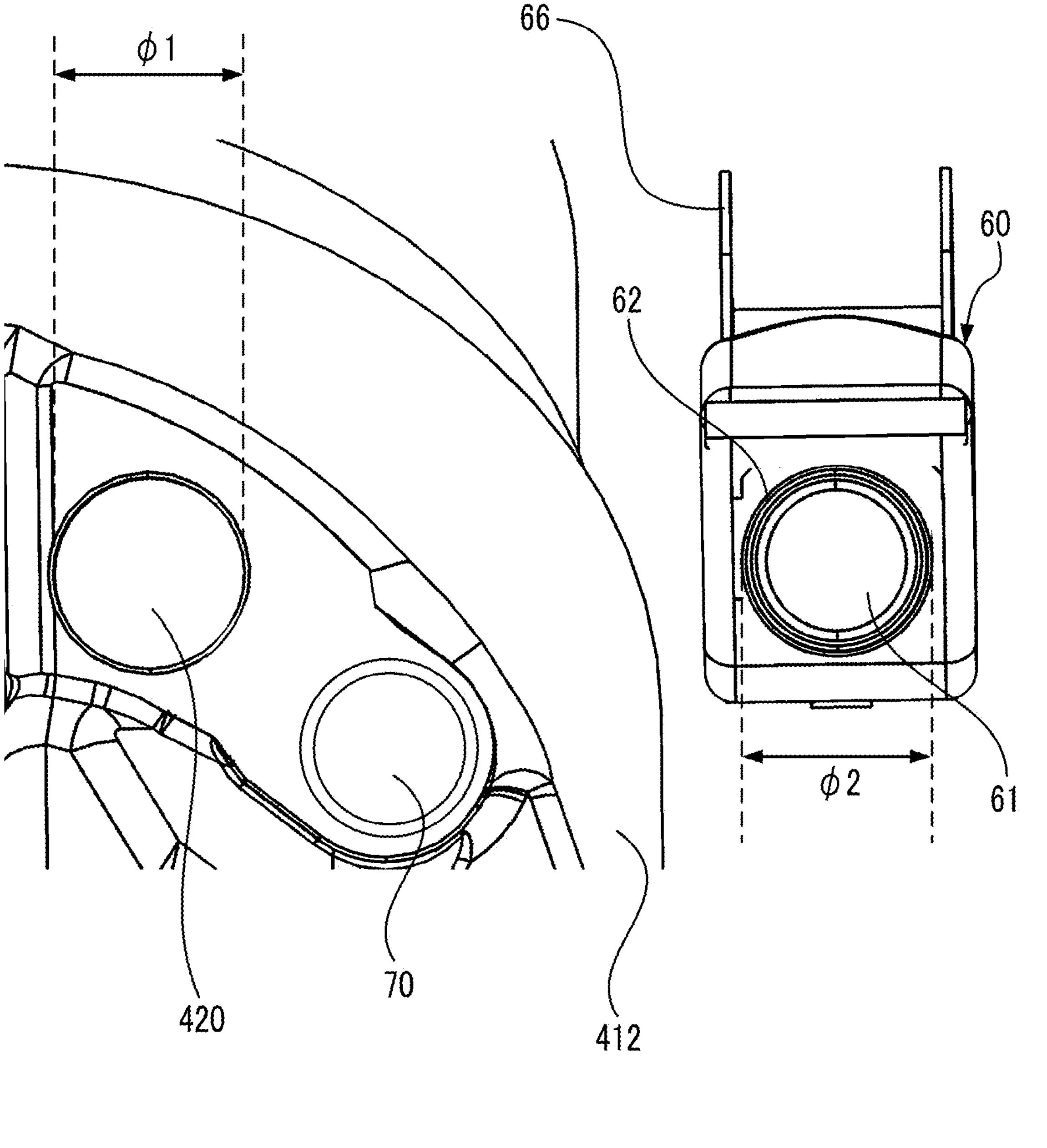
FIG. 14 is a schematic view for describing sizes of a hole portion 420 and a lens barrel 62.

FIG. 14 is a schematic view for describing sizes of the hole portion 420 and the lens barrel 62. FIG. 14 shows a view of the vicinity of the hole portion 420 of the second exterior body 412 as viewed from the distal end side and a view of the imaging module 60 as viewed in an optical axis direction of the observation window 61.

An inner diameter φ1 of the hole portion 420 is larger than an outer diameter φ2 of the lens barrel 62. A value obtained by subtracting the outer diameter φ2 from the inner diameter φ1, that is, a distance between an inner peripheral surface of the hole portion 420 and an outer peripheral surface of the lens barrel 62, is referred to as a second distance. As described above, the second distance is a small value to the extent that the lens barrel 62 cannot be moved in the radial direction but can be rotated in a circumferential direction of the lens barrel 62.

In a case where the lens barrel 62 is rotated in the hole portion 420 in a state where the lens barrel 62 is inserted into the hole portion 420 and is fixed to the hole portion 420, the holder 65 and the cable support part 66 are also moved in conjunction with the lens barrel 62. Therefore, it is necessary to provide a space in which the holder 65 and the cable support part 66 can move in the accommodation space 421.

As shown in FIG. 13, a gap CL is formed between a left wall surface WL and a right wall surface WR forming the accommodation space 421, and the holder 65 and the cable support part 66. A distance (first distance) of the gap CL is larger than the above-described second distance. The left wall surface WL and the right wall surface WR respectively constitute side surfaces surrounding the imaging unit. As shown in FIG. 11, it is preferable that the gap CL is provided on left and right sides of the cable support part 66. With such a configuration, the lens barrel 62 can be rotated by the same amount in either circumferential direction.

As described above, at least the following matters are described in the present specification.

(1)

A system comprising: an ultrasound endoscope including a transducer array in which a plurality of transducers, each of which extends in a first direction intersecting an axial direction of an insertion part of the ultrasound endoscope, are arranged in a curved shape; and a processor configured to perform processing of generating an ultrasound image based on an output signal of the transducer array obtained by controlling the transducer array, in which an opening angle of the transducer array as viewed in the first direction is 90 degrees or more and less than 180 degrees, and the processor is configured to perform first control of generating the ultrasound image with a first angle of view which is larger than the opening angle.

(2)

The system according to (1), in which the opening angle is 140 degrees or more and 160 degrees or less.

(3)

The system according to (1) or (2), in which the first angle of view is greater than the opening angle by 15 degrees or more.

(4)

The system according to any one of (1) to (3), in which the first angle of view is 180 degrees or less.

(5)

The system according to any one of (1) to (4), in which the transducer array is configured such that the transducers are arranged along an arc of a circle, and the processor is configured to perform, in the first control, first driving control of causing an ultrasound beam to propagate in a second direction intersecting a third direction connecting the transducer at a center of a transducer group that generates the ultrasound beam and a center of the circle as viewed in the first direction, on at least a part of the transducer array.

(6)

The system according to (5), in which the processor is configured to perform the first driving control on a region of the transducer array that generates the ultrasound image of at least a part beyond the opening angle.

(7)

The system according to (6), in which the second direction includes a direction toward a proximal end side of the insertion part with respect to the third direction.

(8)

The system according to (6) or (7), in which the second direction includes a direction toward a distal end side of the insertion part with respect to the third direction.

(9)

The system according to any one of (5) to (8), in which the processor is configured to perform, in the first control, second driving control of causing the ultrasound beam to propagate in the third direction as viewed in the first direction, on a part of the transducer array.

(10)

The system according to (9), in which the part of the transducer array subjected to the second driving control is a center portion of the transducer array.

(11)

The system according to (10), in which the center portion is in a range of ±45 degrees from a center of the transducer array.

(12)

The system according to any one of (5) to (11), in which the processor is configured to further perform second control of generating the ultrasound image with a second angle of view smaller than the first angle of view.

(13)

The system according to (12), in which in a case of the second control, the ultrasound beam generated by the transducer group that generates an ultrasound beam corresponding to an end edge of the ultrasound image propagates more toward a center side of the transducer array compared to a case of the first control.

(14)

The system according to (13), in which an intersection point of an extension line of a line connecting a transmission focal point of the ultrasound beam generated by the transducer group that generates an ultrasound beam corresponding to both end edges of the ultrasound image and the transducer at the center of the transducer group is located closer to a propagation direction side of the ultrasound beam in the case of the first control than in the case of the second control.

(15)

The system according to any one of (1) to (14), in which the number of channels of the transducer array is 96 or more and 128 or less.

(16)

The system according to any one of (1) to (15), in which the ultrasound endoscope has an observation window provided on a proximal end side with respect to the transducer array, the transducer array is configured such that the transducers are arranged along an arc of a circle, the observation window is provided to be inclined with respect to an axis of the insertion part as viewed in the first direction, and a first angle formed by a straight line connecting a center of the circle and the transducer at an end in the transducer array on the proximal end side of the insertion part and the axis is equal to or greater than a second angle formed by the observation window and the axis.

(17)

The system according to (16), in which the second angle is equal to or greater than a third angle formed by a propagation direction of a first ultrasound beam at the end on the proximal end side of the insertion part generated from the transducer array in a case of performing the first control and the axial direction, as viewed in the first direction.

(18)

The system according to (17), in which, as viewed in the first direction, the third angle is an angle at which a straight line extending from the transducer at a center of a transducer group that generates the first ultrasound beam in the transducer array in the propagation direction does not intersect the observation window.

(19)

The system according to (17) or (18), in which a fourth angle formed by a straight line connecting the center of the circle and a center of the transducer array and the axis is 45 degrees or more and 55 degrees or less, and the second angle is 35 degrees or more and 50 degrees or less.

(20)

The system according to any one of (1) to (19), in which the ultrasound endoscope has an observation window provided on a proximal end side with respect to the transducer array, and as viewed in the first direction, one end edge of the transducer array in a direction perpendicular to an axis of the insertion part is included in an observation visual field of the observation window.

(21)

The system according to (20), in which a center of the transducer array is included between rays that constitute both ends of the observation visual field of the observation window as viewed in the first direction.

(22)

The system according to (20) or (21), in which a center of the observation visual field is located on a side opposite to the axis with respect to the one end edge as viewed in the first direction.

(23)

The system according to any one of (20) to (22), in which the ultrasound endoscope includes an imaging module that includes an imaging optical system including the observation window and an imaging unit that performs imaging through the imaging optical system, and a support member that supports the imaging optical system and the imaging unit, the support member includes a hole portion into which the imaging optical system is inserted and a side surface that surrounds the imaging unit, and a gap is formed between the side surface and the imaging unit.

(24)

The system according to (23), in which a first distance of the gap is larger than a second distance between an inner peripheral surface of the hole portion and an outer peripheral surface of the imaging optical system.

(25)

The system according to (24), in which a position of the imaging optical system in a direction perpendicular to an optical axis is positioned at the hole portion.

(26)

The system according to any one of (20) to (25), in which a distance in the axial direction between an end edge in the transducer array on the proximal end side of the insertion part and the observation window is 10 mm or less.

(27)

The system according to any one of (20) to (26), in which the ultrasound endoscope has an illumination window provided on the proximal end side with respect to the transducer array, and a center line of the illumination window is located on a side opposite to the axis with respect to the one end edge as viewed in the first direction.

(28)

The system according to (27), in which the observation window and the illumination window are provided eccentric to the same direction as viewed in the axial direction.

(29)

The system according to (28), in which the ultrasound endoscope has an outlet port of a treatment tool, and the transducer array, the observation window, and the outlet port are provided in this order from a distal end side of the ultrasound endoscope.

EXPLANATION OF REFERENCES

10: ultrasound examination system
12: ultrasound endoscope
14: ultrasound processor device
16: endoscope processor device
18: light source device
20: monitor
21*a*: water supply tank
21*b*: suction pump
22: insertion part
24: operating part
26: universal cord
28*a*: air/water supply button
28*b*: suction button
29: angle knob
30: treatment tool insertion port
32*a*, 32*b*, 32*c*: connector
34*a*: air/water supply tube
34*b*: suction tube
36: ultrasound observation part
38: optical observation part
40: distal end part
40X: axis
42: bendable part
43: flexible part
50: transducer array
50A: angle
50C: center
50F: transmission focal point
50L: straight line
50R: reception data group
50T: ultrasound beam
50U: upper end edge
50*r*: reception data
51: transducer
51G: transducer group
52: center of curvature
52A: intersection
60: imaging module
61: observation window
61A: observation range upper limit
61B: observation range lower limit
61C: optical axis
62: lens barrel
63: prism
64: imaging element
65: holder
66: cable support part
70: illumination window
70C: center line
80: signal cable
90: raising base
91: treatment tool insertion path
91A: outlet port
411: first exterior body
412: second exterior body
412A: distal end surface
412B: recess portion
412D: lower member
412U: upper member
420: hole portion
421: accommodation space
500, 501: ultrasound image
500A, 501A: angle of view
500Rr, 500Fr, 501Rr, 501Fr: image line
610: observation visual field
D1: distance
L1, L2, L3, L4: straight line
E1: one end edge
E2: the other end edge

What is claimed is:

1. An ultrasound endoscope system comprising:

an ultrasound endoscope including a transducer array in which a plurality of transducers, each of which extends in a first direction intersecting an axial direction of an insertion part of the ultrasound endoscope, are arranged in a curved shape; and a processor configured to perform processing of generating an ultrasound image based on an output signal of the transducer array obtained by controlling the transducer array, wherein an opening angle of the transducer array as viewed in the first direction is 90 degrees or more and less than 180 degrees, and the processor is configured to perform first control of generating the ultrasound image with a first angle of view which is larger than the opening angle, wherein the ultrasound endoscope has an observation window provided on a proximal end side with respect to the transducer array, as viewed in the first direction, one end edge of the transducer array in a direction perpendicular to an axis of the insertion part is included in an observation visual field of the observation window, wherein a center of the transducer array is included between rays that constitute both ends of the observation visual field of the observation window as viewed in the first direction, wherein a center of the observation visual field is located on a side opposite to the axis with respect to the one end edge as viewed in the first direction, wherein the ultrasound endoscope includes an imaging module that includes an imaging optical system including the observation window and an imaging unit that performs imaging through the imaging optical system, and a support member that supports the imaging optical system and the imaging unit, the support member includes a hole portion into which the imaging optical system is inserted and a side surface that surrounds the imaging unit, a gap is formed between the side surface and the imaging unit, and wherein the gap is configured to allow the processor to be configured to control the imaging unit to be rotatable around an optical axis of the observation window within the hole portion to adjust a position of the transducer array in a captured image captured by the imaging unit.

2. The ultrasound endoscope system according to claim 1, wherein the opening angle is 140 degrees or more and 160 degrees or less.

3. The ultrasound endoscope system according to claim 2, wherein the first angle of view is greater than the opening angle by 15 degrees or more.

4. The ultrasound endoscope system according to claim 3, wherein the first angle of view is 180 degrees or less.

5. The ultrasound endoscope system according to claim 1, wherein the transducer array is configured such that the transducers are arranged along an arc of a circle, and the processor is configured to perform, in the first control, first driving control of causing an ultrasound beam to propagate in a second direction intersecting a third direction connecting a transducer at a center of a transducer group that generates the ultrasound beam and a center of the circle as viewed in the first direction, on at least a part of the transducer array.

6. The ultrasound endoscope system according to claim 5, wherein the processor is configured to perform the first driving control on a region of the transducer array that generates the ultrasound image of at least a part beyond the opening angle.

7. The ultrasound endoscope system according to claim 6, wherein the second direction includes a direction toward a proximal end side of the insertion part with respect to the third direction.

8. The ultrasound endoscope system according to claim 7, wherein the second direction includes a direction toward a distal end side of the insertion part with respect to the third direction.

9. The ultrasound endoscope system according to claim 5, wherein the processor is configured to perform, in the first control, second driving control of causing the ultrasound beam to propagate in the third direction as viewed in the first direction, on a part of the transducer array.

10. The ultrasound endoscope system according to claim 9, wherein the part of the transducer array subjected to the second driving control is a center portion of the transducer array.

11. The ultrasound endoscope system according to claim 10, wherein the center portion is in a range of ±45 degrees from the center of the transducer array.

12. The ultrasound endoscope system according to claim 5, wherein the processor is configured to further perform second control of generating the ultrasound image with a second angle of view smaller than the first angle of view.

13. The ultrasound endoscope system according to claim 12, wherein in a case of the second control, the ultrasound beam generated by the transducer group that generates an ultrasound beam corresponding to an end edge of the ultrasound image propagates more toward a center side of the transducer array compared to a case of the first control.

14. The ultrasound endoscope system according to claim 13, wherein an intersection point of an extension line of a line connecting a transmission focal point of the ultrasound beam generated by the transducer group that generates an ultrasound beam corresponding to both end edges of the ultrasound image and the transducer at a center of the transducer group is located closer to a propagation direction side of the ultrasound beam in the case of the first control than in the case of the second control.

15. The ultrasound endoscope system according to claim 5, wherein number of channels of the transducer array is 96 or more and 128 or less.

16. The ultrasound endoscope system according to claim 1, the transducer array is configured such that the transducers are arranged along an arc of a circle, the observation window is provided to be inclined with respect to the axis of the insertion part as viewed in the first direction, and a first angle formed by a straight line connecting a center of the circle and the transducer at an end in the transducer array on the proximal end side of the insertion part and the axis is equal to or greater than a second angle formed by the observation window and the axis.

17. The ultrasound endoscope system according to claim 16, wherein the second angle is equal to or greater than a third angle formed by a propagation direction of a first ultrasound beam at the end on the proximal end side of the insertion part generated from the transducer array in a case of performing the first control and the axial direction, as viewed in the first direction.

18. The ultrasound endoscope system according to claim 17, wherein, as viewed in the first direction, the third angle is an angle at which a straight line extending from the transducer at a center of a transducer group that generates the first ultrasound beam in the transducer array in the propagation direction does not intersect the observation window.

19. The ultrasound endoscope system according to claim 18, wherein a fourth angle formed by a straight line connecting the center of the circle and the center of the transducer array and the axis is 45 degrees or more and 55 degrees or less, and the second angle is 35 degrees or more and 50 degrees or less.

20. The ultrasound endoscope system according to claim 1, wherein a first distance of the gap is larger than a second distance between an inner peripheral surface of the hole portion and an outer peripheral surface of the imaging optical system.

21. The ultrasound endoscope system according to claim 20, wherein a position of the imaging optical system in a direction perpendicular to an optical axis is positioned at the hole portion.

22. The ultrasound endoscope system according to claim 21, wherein a distance in the axial direction between an end edge in the transducer array on the proximal end side of the insertion part and the observation window is 10 mm or less.

23. The ultrasound endoscope system according to claim 22, wherein the ultrasound endoscope has an illumination window provided on the proximal end side with respect to the transducer array, and a center line of the illumination window is located on the side opposite to the axis with respect to the one end edge as viewed in the first direction.

24. The ultrasound endoscope system according to claim 23, wherein the observation window and the illumination window are provided eccentric to a same direction as viewed in the axial direction.

25. The ultrasound endoscope system according to claim 24, wherein the ultrasound endoscope has an outlet port of a treatment tool, and the transducer array, the observation window and the outlet port are provided in this order from a distal end side of the ultrasound endoscope.

* * * * *